(12) United States Patent
Flagg et al.

(10) Patent No.: US 6,978,179 B1
(45) Date of Patent: Dec. 20, 2005

(54) METHOD AND APPARATUS FOR MAGNETIC BRAIN WAVE STIMULATION

(76) Inventors: Rodger H. Flagg, 10504 Daysailer Dr., Fairfax Station, VA (US) 22039; W. Bruce Barham, 1276 N. Wayne St. #902, Arlington, VA (US) 22201; Deborah Anne Stokes, 5933 Wilton Rd., Alexandria, VA (US) 22310; Glen Elliot Kotapish, 1002 Wilson Point Rd., Apt. E, Middle River, MD (US) 21220

( * ) Notice: Subject to any disclaimer, the term of this patent is extended or adjusted under 35 U.S.C. 154(b) by 471 days.

(21) Appl. No.: 10/372,924

(22) Filed: Feb. 26, 2003

Related U.S. Application Data

(60) Provisional application No. 60/359,636, filed on Feb. 27, 2002.

(51) Int. Cl.[7] ................................................ A61N 1/10
(52) U.S. Cl. ...................................................... 607/45
(58) Field of Search .............................. 607/45, 63–71, 607/75; 600/544, 545; 434/236

(56) References Cited

U.S. PATENT DOCUMENTS 4,736,751 A * 4/1988 Gevins et al. ............... 600/545
6,457,975 B1 * 10/2002 Miranda et al. ............ 434/236
6,626,676 B2 * 9/2003 Freer .......................... 434/236

* cited by examiner

Primary Examiner—George Manuel

(57) ABSTRACT

The present invention relates to a streamlined magnetic brain wave stimulation apparatus, which receives electronic signals based upon pre-recorded brain wave patterns. The brain wave patterns actuate electromagnets placed on a user's neck adjacent to the user's brainstem, to create a plurality of magnetic pulses to influence a user's brain centers to influence a desired mental state. Rhythmic electrical brain wave signals are recorded, identified, divided and repeated to create a streamlined brain wave signal to induce a desired mental state. The streamlined patterns are then recorded on a suitable memory means. When the memory means is actuated, the rhythmic electrical signals are sent to electromagnets located in proximity to the back of the user's neck in proximity to the posterior aspect of the user's superior cervical region, in an area that is immediately inferior to the cranial cavity to electromagnetically stimulate the brain stem, to influence a desired mental state. This produces a gentle magnetic stimulation, which is neither felt nor discerned by the user. The gentle magnetic stimulation passes through the brain stem to the brain centers to influence the desired mental state.

23 Claims, 8 Drawing Sheets

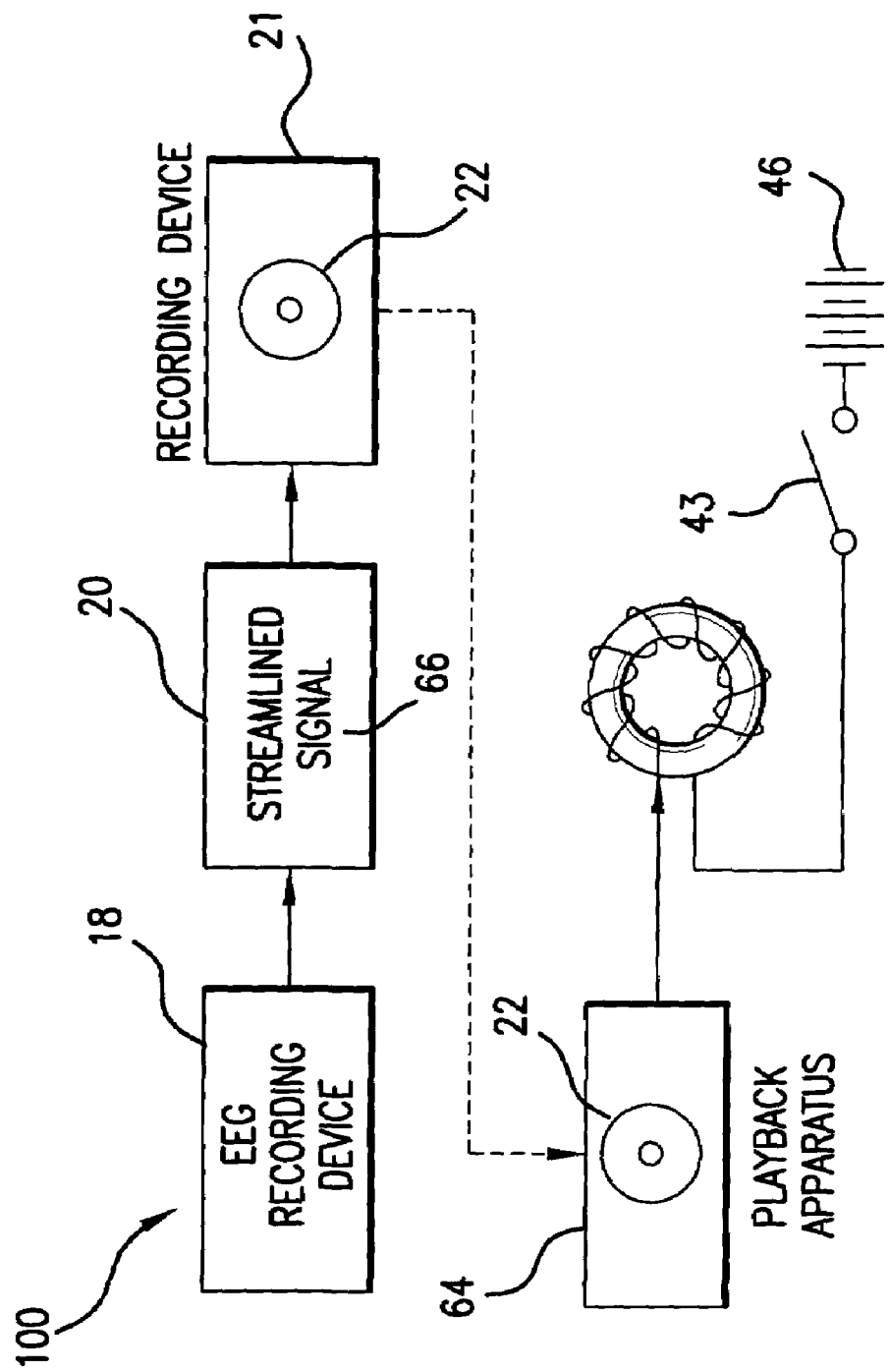

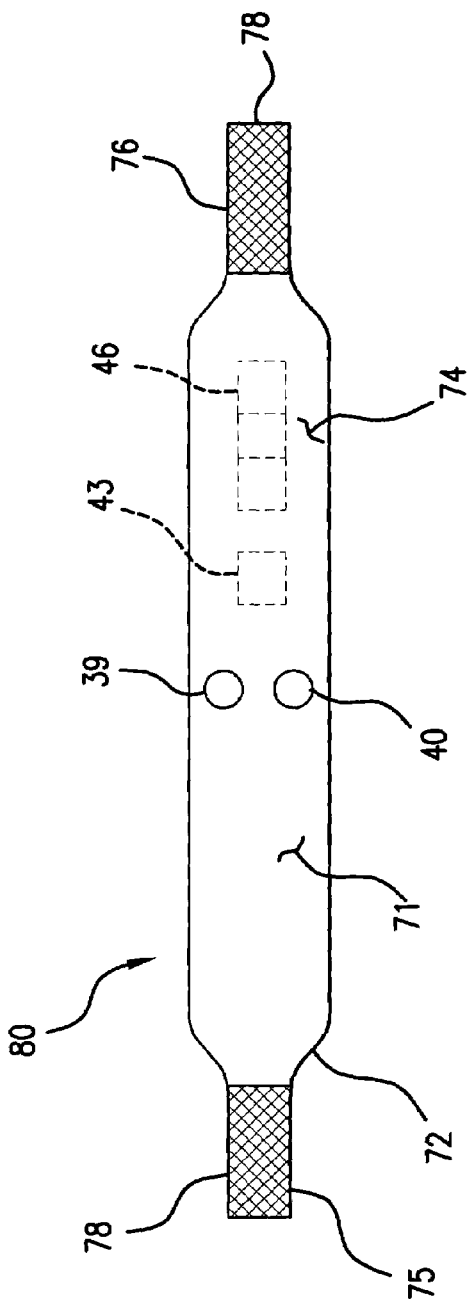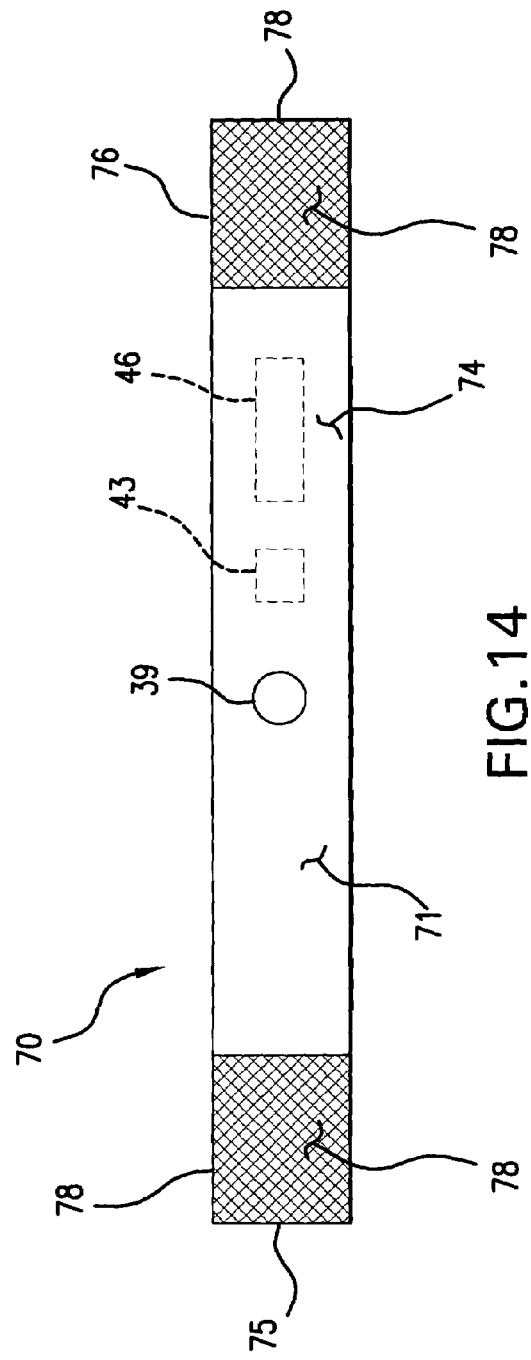

METHOD AND APPARATUS FOR MAGNETIC BRAIN WAVE STIMULATION

This patent application claims priority of provisional patent application 60/359,636 filed Feb. 27, 2002, entitled: MAGNETIC BRAIN WAVE STIMULATION APPARATUS, by Rodger H. Flagg et al. Said provisional patent application is incorporated by reference herein.

BACKGROUND OF THE INVENTION

This invention relates to a brain wave stimulation apparatus, and more particularly to a method and apparatus for streamlined magnetic brain wave stimulation, recorded as a brain wave signal and sent to an electromagnet positioned on a user's neck in proximity to the user's brain stem to positively influence a user's brain wave pattern, to produce a desired mental state.

1. Field of the Invention

Electroencephalography (EEG) records the neural activity of electrical potential across cell membranes, which are detected through the cortex and recorded by a plurality of scalp electrodes. The changes in electrical potential in the cortex contain rhythmical activity, which typically occur at frequencies of 1 Hz to 20 Hz. While awake, fast, random signals are predominately generated at low voltage and mixed frequency.

Four distinct brain wave patterns are commonly detected during an EEG recording: Alpha waves, beta waves, theta waves and delta waves.

Magnetoencephalography (MEG) records tiny magnetic fields, which are oriented at right angles to the electrical fields of the brain. Thus, the membrane potential of neurons during normal activity is mirrored by complementary tangentially flowing magnetic fields. These magnetic fields may be altered by transcranial magnetic stimulation (TMS).

Transcranial Magnetic Stimulation (TMS) involves placing a coil that generates a strong magnetic field near the user's head. The magnetic field induces a small electrical current in the outer layers of the brain, causing nerve cells to fire, setting off various chemical changes in the brain.

2. Description of the Prior Art

U.S. Pat. No. 6,314,324 issuing Nov. 6, 2001 to Stefanic Lattner et al. discloses a vestibular stimulation system utilizing a predetermined pattern of stimulation about a user's ear.

U.S. Pat. No. 6,272,378 issuing on Aug. 7, 2001 to Rudolf Baumgart-Schmitt et al. discloses a device for determining sleep profiles having an active electrode positioned symmetrical to the nose root, and utilizing a compressed EEG signal to induce sleep.

U.S. Pat. No. 6,081,743 issuing on Jun. 27, 2000 to John Carter et al. discloses a method for obtaining a brain wave frequency from an individual by EEG, and transcranially feeding back the highest evoked response at an output detectable by the individual for a specified period of time.

U.S. Pat. No. 5,899,922 issuing on May 4, 1999 to Hendricus Loos discloses the manipulation of a user's nervous system by use of electrical fields.

U.S. Pat. No. 5,356,368 issuing on Oct. 18, 1994 to Robert Monroe discloses a method of inducing a desired state of consciousness employing frequency following response techniques, to induce sleep or a desired level of consciousness.

U.S. Pat. No. 5,241,967 issuing on Sep. 7, 1993 to Mitsuo Yasushi et al, discloses a system for evoking EEM signals utilizing electrodes attached to the scalp, and a stimulus generator to convert the frequency of the signal to a photic or audible stimulating signal.

U.S. Pat. No. 4,503,863 issuing Mar. 12, 1985 to Jefferson Katims discloses a method and apparatus for transcutaneous electrical stimulation utilizing a constant current output in response to an actual EEG signal.

U.S. Pat. No. 3,762,396 issuing Oct. 2, 1973 to Earle Ballentine discloses a method and apparatus for inducing sleep by applying electrical pulses to plural portions of the back of the head and forehead, the optic nerve, the temples, the forehead, and the ears.

U.S. Pat. No. 3,718,132 issuing Feb. 27, 1973 to William Holt et al, discloses an electrotherapy machine utilizing repetitive alternating positive and negative electrical pulses having a vectorial sum of zero.

U.S. Pat. No. 3,835,833 issuing Sep. 17, 1974 to Aime Limoge, discloses a method for determining neurophysiological effects utilizing a first signal utilizing square shaped pulses, and a second signal generated by a white noise spectrum.

U.S. Pat. No. 3,648,708 issuing Mar. 14, 1972 to Mehdi Haeri discloses an electrical therapeutic device utilizing a pulse generator, a current regulator and a metering circuit. The resulting electrical signal is applied to various portions of the user's anatomy.

U.S. Pat. No. 3,495,596 issuing Feb. 17, 1970 to E. Condict discloses a method and apparatus for processing a bioelectrical signal to induce anesthesia.

U.S. Pat. No. 3,464,416 discloses a sleep inducing method utilizing a headpiece extending from the forehead to the occipital region of the head, and generating electrical signals of 36 cps.

U.S. Pat. No. 3,388,699 issuing Jun. 18, 1968 to M. Webb et al, discloses a method and apparatus for inducing lethargic relation or sleep, by applying electrical current to the eyelids and mastoid regions.

U.S. Pat. No. 3,160,159 issuing Dec. 8, 1964 to J. Hoody et al discloses a device for inducing sleep utilizing pulsed electrodes.

The following U.S. Patents disclose multiple sources of electrical stimulation, such as heat, light, sound and VHF radiation. They include 5,954,629; 5,719,635; 5,495,853; 4,227,516; 4,305,402; 4,018,218; 3,773,049 and Re. 36,348.

The following U.S. Patents utilize sound to stimulate the brain. They include: 5,954,630; 5,289,438; 5,213,562; 5,151,080; 5,036,858; 4,883,067; 4,834,701; 4,335,710; 4,141,344; 3,884,218; 3,753,433; and 3,712,292.

Other patents of interest include: 6,135,944; 5,167,610; 4,418,687; 3,103,219 and 3,014,477.

These patents disclose and claim various methods and apparatus for inducing a desired mental state, such as: inducing sleep or a relaxed state, by utilizing various means of stimulating the brain by visual, audible or electronic stimulation to the eyes, ears, scalp, back of the head, forehead, temples, or nose root.

SUMMARY OF THE INVENTION

The present patent application discloses an improved method and apparatus, utilizing one or more electromagnets positioned in proximity to the posterior aspect of the user's superior cervical region, in an area that is immediately inferior to the cranial cavity to electromagnetically stimulate the brain stem, to influence a desired mental state, such as sleep, a calm and relaxing state, a creative state, or a stimulated state.

Electrical signals contain rhythmic changes in electric potential resulting from bioelectric activity in the brain. These brain wave patterns are typically recorded as delta, theta, alpha and, beta brain wave patterns which are obtained from electrodes selectively positioned about the user's skull.

Applicant's invention utilizes one or more electrode sensor(s) positioned upon the user's neck to pre-record the electrical signal(s) generated by the electrode sensor(s). The pre-recorded signal is then remotely streamlined, recorded and then selectively play back on demand to influence a desired mental state.

One or more electromagnet(s) are positioned about the user's neck in proximity to the user's brain stem to influence the desired mental state. The recorded streamlined brain wave signals are sent from the streamlined recorded signal to selectively energize one or more electromagnets. The electromagnets are energized by a power means responsive to the pulsed electrical signal received from the recorded streamlined brain wave singal(s), to produce a plurality of magnetic signal pulses corresponding to the streamlined signal generated by the recorded streamlined brain wave patterns. The electromagnetic coil(s) are positioned adjacent to the user's skin on a user's neck in a region adjacent to the brain stem in close proximity to the posterior aspect of the user's superior cervical region, in an area that is immediately inferior to the cranial cavity. The electromagnetic coil(s) are actuated to create a plurality of low energy magnetic pulses, similar to the magnetic pulses generated by an electromagnetic coil used in a conventional cell phone. The low energy magnetic pulses pass through the user's skin to the brainstem, and from the brainstem to the brain control centers, to gently influence a desired mental state.

EEG brain wave signals are typically recorded as delta (0.5–3 Hz), theta (4–8 Hz), alpha (8–12 Hz), and beta (13–20 Hz) brain wave signals. At times, spikes of up to 45 Hz occur during the dream state. These EEG brain wave signals are typically obtained by positioning electrodes upon the user's skull. The streamlined brain wave pattern may be divided into slow wave patterns (Delta waves and Theta waves) and (Alpha waves and Beta waves).

In contrast, the present invention records the bioelectric signal at a location on the user's neck near the posterior aspect of the user's superior cervical region, in an area that is immediately inferior to the cranial cavity to electromagnetically stimulate the brain stem, to gently influence a desired mental state. This bioelectric signal is not identical to the multiple EEG signals generated at various selected regions of the user's skull.

The electromagnet becomes weaker or stronger as the voltage to the electromagnet varies. For example, the earpiece in a telephone comprises an electromagnet with a ferrous core. The stronger the current, the further the ferrous core moves, to create soundwaves of different frequencies. Thus one electromagnet may transmit over a range exceeding 0.1 to 50 Hz, or cycles per second, much as an orchestra transmits sound waves from numerous instruments, which are simultaneously audibly or digitally recorded and played back as audible sounds.

The streamlined brain wave patterns are then preferably selectively transmitted, by one or more wireless transmitting means, to a complimentary receiver means located upon the neck apparatus. The received electrical signals, are then sent as pulsed electrical signals to the respective electromagnet(s) located on the neck apparatus, to create a streamlined magnetic pulse.

Alternately, the recorded streamlined brain wave patterns are sent directly to the electromagnet(s) to create a streamlined magnetic pulse. The streamlined magnetic pulses are non-invasive, and serve to gently influence one or more portions of the brain center, to influence a desired mental state. A single electromagnet is shown in FIG. 12.

When two electromagnets are used, the first and second electromagnets are positioned adjacent to the user's neck, near the user's skin, preferably one on each side of the brain stem or centered one above the other, over the brainstem in close proximity to the posterior aspect of the user's superior cervical region, in an area that is immediately inferior to the cranial cavity, as shown in FIG. 9. This transmits a gentle, non-invasive magnetic signal, which is neither felt nor discerned through the user's neck skin, to the brain stem, which directs the streamlined magnetic signal to various portions of the brain center to influence the desired mental state. The brain centers serve to modulate and control the user's mental state, including, but not limited to: a sleep state, a calm and relaxing state, a creative state, or a stimulated state.

When four electromagnets are used, two of the electromagnets are preferably positioned adjacent to one side of the brain stem, and two electromagnets are preferably positioned adjacent to the opposite side of the brain stem, in close proximity to the posterior aspect of the user's superior cervical region, in an area that is immediately inferior to the cranial cavity.

The magnetic brain wave stimulation apparatus disclosed herein, will be best understood by reference to the following specification, when taken in conjunction with the following drawings.

BRIEF DESCRIPTION OF THE DRAWINGS

FIG. 12 is a block diagram showing a playback apparatus for sending a streamlined signal from a memory means directly to an electromagnet.

FIG. 13 is a plan view of the neck apparatus with two vertically aligned electromagnets.

FIG. 14 is a plan view of the neck apparatus with a single electromagnet.

One object of the present invention is to provide a method and apparatus for an improved brain wave stimulation apparatus, designed to provide a magnetic signal in proximity to the brain stem to influence a desired mental state.

Another object is to transform an electrical signal to a magnetic signal through use of at least one electromagnet positioned adjacent to a user's neck in proximity to the user's brain stem at a location in close proximity to the posterior aspect of the user's superior cervical region, in an area that is immediately inferior to the cranial cavity.

Yet another object is to receive and record a bioelectric signal from a user in proximity to the brain stem during a desired mental state, to streamline the signal, and to selectively transmit the streamlined signal back to the user on demand to influence a desired mental state.

Still another object is to provide a streamlined magnetic brain wave stimulation apparatus, wherein a pre-recorded brain wave signal is streamlined, recorded, and sent to at least one electromagnet located on a neck pad positioned about a user's neck in proximity to the brain stem and adjacent to the posterior aspect of the user's superior cervical region, in an area that is immediately inferior to the cranial cavity to electromagnetically stimulate the brain stem, to influence a desired mental state.

Another object is to provide a streamlined brain wave signal selected to induce a desired mental state, such as sleep, a calm and relaxing state, a creative state, or a stimulated state.

Other objects will be apparent when reviewing the entire specification, drawings and claims found herein.

DESCRIPTION OF THE PREFERRED EMBODIMENT

Figure 1:
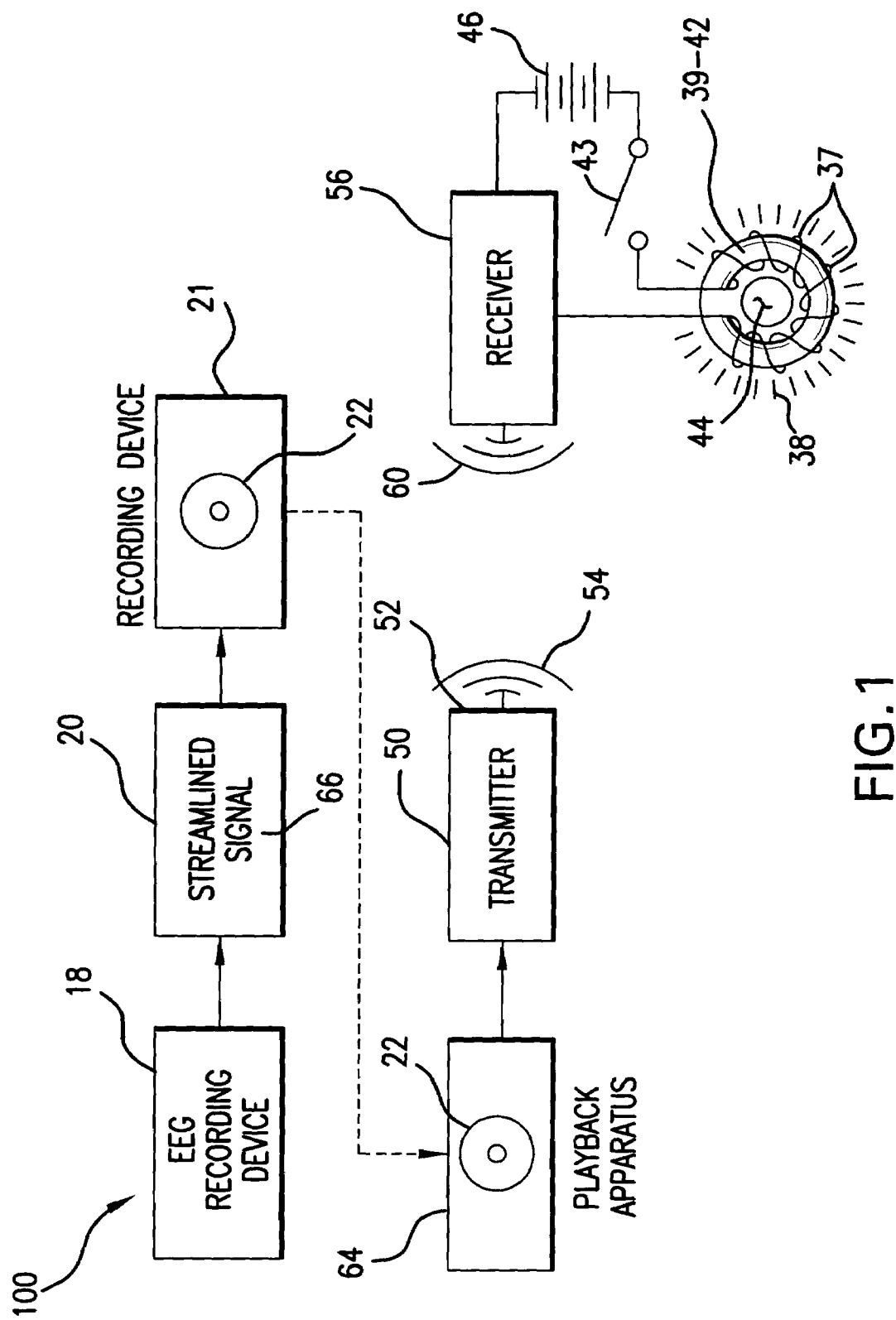
FIG. 1 is a block diagram showing the use of a transmitter and receiver for sending a streamlined signal to at least one electromagnet.

FIG. 1 is a block diagram showing a preferred embodiment of the various component parts of the streamlined magnetic brain wave stimulation apparatus 100. As shown in FIG. 1, a selected user's brain wave pattern 20 is first recorded by an electronic sensor, or other known sensor means 18, positioned on the user's neck 14 near the brain stem 24 proximate to the posterior aspect of the user's superior cervical region, in an area that is immediately inferior to the cranial cavity. The signal from the electronic sensor 18 is then recorded, and streamlined to create a streamlined brain wave pattern 20.

The streamlined brain wave pattern 20 is stored upon a suitable memory or recording apparatus, hereafter memory means 22 and played back on demand to influence a desired mental state. The signal from the memory means 22 is sent to one or more electromagnet(s) 39 located upon the user's neck in proximity to the brain stem 24 to electromagnetically stimulate the brain stem, to influence a desired mental state. As previously noted, the streamlined brain wave pattern 20 is recorded by a suitable recording means 21, and stored for later use upon a suitable memory means 22.

Figure 11A:
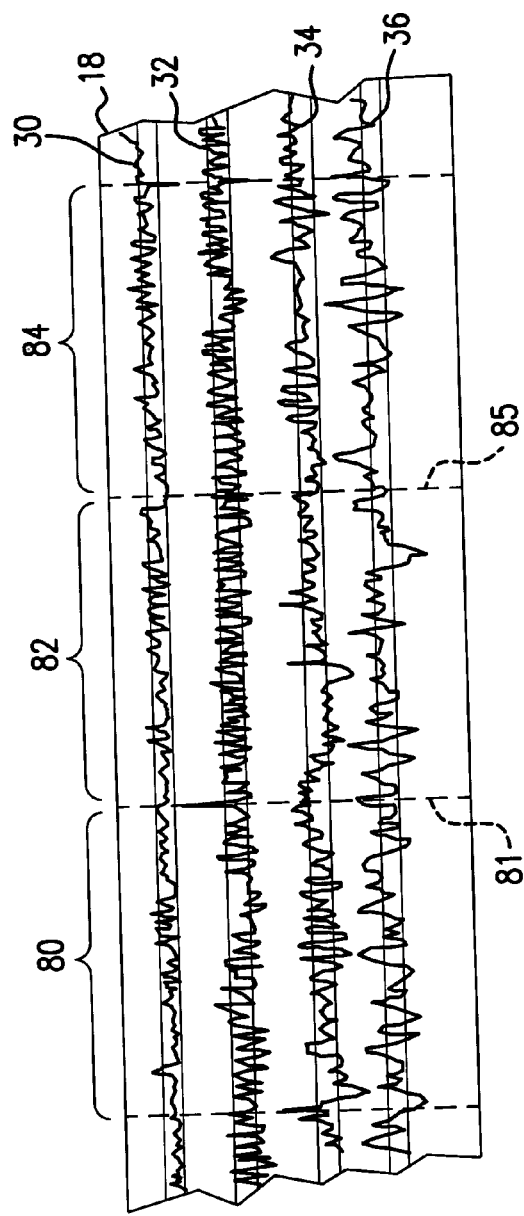
FIG. 11A is a schematic view of a pre-recorded segment of the brain wave pattern prior to streamlining.
Figure 11B:
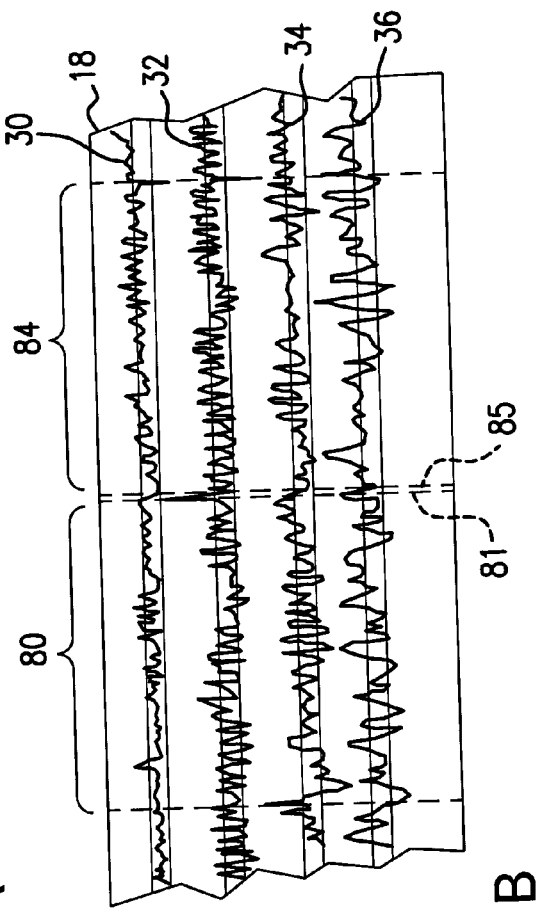
FIG. 11B is a schematic view of a pre-recorded segment of the brain wave pattern after streamlining.

The recorded brain wave pattern 20 may be streamlined by a cut and paste technique, as shown in FIGS. 11A and 11B. The cut and paste technique saves a first piece of signal data 80 (at least two continuous data signal cycles, and preferably more than six continuous data signal cycles), deletes a second piece of data 82 (at least two continuous data signal cycles, and preferably more than six continuous data signal cycles), and saves a third piece of data 84 (at least two continuous data signal cycles, and preferably more than six continuous data signal cycles). The end 81 of the first piece of saved data 80 is then spliced or joined to the start 85 of the third piece of saved data 84, and the second piece of data 82 is deleted from the streamlined brain wave pattern 20. This streamlining technique 20 provides a means to selectively delete, repeat and store a plurality of data signals for a selected duration.

The streamlined brain wave pattern 20 may also be accomplished electronically, by selectively turning a recording device off and on during the streamlined recording of the brain wave pattern 20. Preferably, the brain wave pattern is first analyzed to identify and isolate a desired signal portion of the brain wave signal, and the desired brain wave signal repeatedly recorded on a memory means 22, and then selectively repeated and/or deleted to create a streamlined brain wave pattern 20 designed to positively influence the desired mental state.

Preferably, the resulting streamlined brain wave pattern 20 selectively incorporates and deletes multiple brain wave signal segments which each include simultaneous portions of the previously recorded 0.1 Hz to 45 Hz brain wave segments. These simultaneous portions of brain wave signal segments are then streamlined 20 to work together to influence the desired mental state.

This streamlined 20 technique is repeated throughout the normal brain wave cycle, until the desired length of memory has been streamlined 20 and recorded by the recording means 21. A suitable memory means 22 stores the streamlined brain wave pattern 20 for playback when desired. The streamlining technique disclosed herein, selectively deletes selected brain wave data, while repeating selected brain wave data to obtain a streamlined brain wave pattern 20, while maintaining whole selected segments of the brain wave patterns in the sequence they naturally occur.

The streamlined brain wave pattern 20 is stored on a suitable memory means 22, including, but not limited to, a memory stick, a computer disc, a cassette, a computer program, an optical storage means, an audible storage means, a digital recording, etc. The streamlined brain wave pattern 20 may then be played back from the memory means 22 and transmitted to one or more electromagnet(s) 39–42 located upon the user's neck 25 near the brain stem 24 in proximity to the posterior aspect of the user's superior cervical region, in an area that is immediately inferior to the cranial cavity to electromagnetically stimulate the brain stem, to influence a desired mental state upon demand.

It is important to note that this streamlining process 20 is significantly different than conventional compression techniques. For example, an eight hour sleep cycle, when compressed by conventional compression techniques, to two hours (4:1), would alter an eight cycle per second alpha brain wave pattern four to one, or to a two cycle per second delta wave brain wave pattern. By streamlining 20 the brain wave pattern as disclosed herein, the 0.1 Hz to 45 Hz brain wave patterns remain intact and distinct from one another, while the overall duration of the sleep cycle is significantly reduced from eight hours to a two to three hour streamlined sleep cycle.

The memory means 22 records and stores the streamlined brain wave pattern 20 generated by the electrical signal previously recorded by the electrode sensor 15 positioned upon the user's neck near the brain stem 24 at a location adjacent to the posterior aspect of the user's superior cervical region, in an area that is immediately inferior to the cranial cavity to electromagnetically stimulate the brain stem, to influence a desired mental state.

When the pre-recorded streamlined brain wave pattern 20 is used to influence a sleep state, this streamlined pattern 20 preferably shortens a user's sleep cycle to at least one half the user's normal sleep pattern, while maintaining the four distinct stages of sleep. The streamlined 20 pattern preferably includes selected portions of the pre-recorded brain wave pattern from 0.1 Hz to 45 Hz, which has been streamlined from a state of alertness through the four recognized stages of a normal sleep cycle.

Multiple electrode brain recordings 18 from multiple selected user's may be selectively combined, prior to streamlining 20, to influence a selected mental state. However, individual brain wave patterns are preferably individually recorded and streamlined 20 for each user, to ensure individual compatibility.

Each user's brain wave pattern is unique, and alters over time. Preferably, the user's streamlined brain wave pattern includes an individual, protectively coded means 66, such as an encryption means, to ensure use only by the selected user. This protectively coded means 66 may be similar to any known security means or encryption means known in the art, and thus is not further detailed herein.

Figure 3:
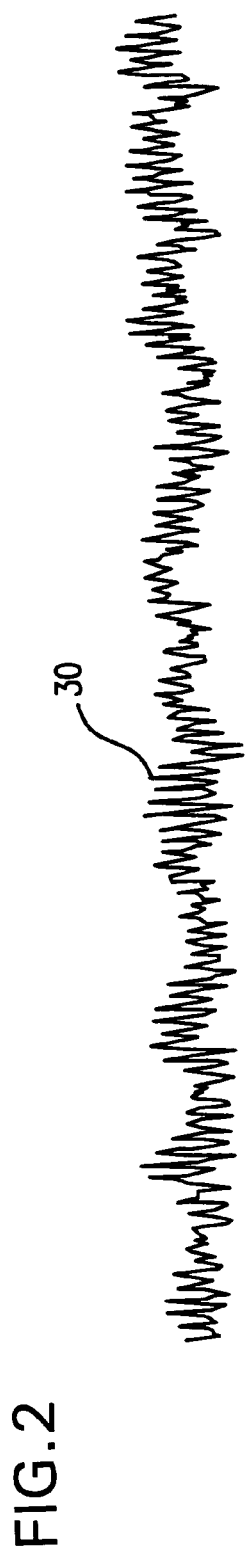
FIG. 3 is a schematic view of a portion of an Alpha brain wave pattern of 8–12 Hz, taken adjacent to the user's skull when the user is in a drowsy condition.
Figure 5:
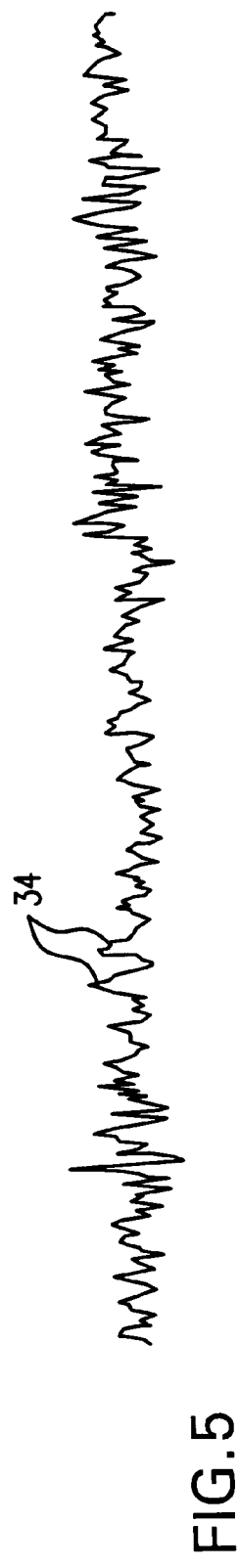
FIG. 5 is a schematic view of a portion of a Theta brain wave pattern of 4 to 7 Hz, taken adjacent to the user's skull, showing sleepy type theta waves.
Figure 6:
FIG. 6 is a schematic view of a portion of a Delta brain wave pattern of 0.5 to 3 Hz, taken adjacent to the user's skull, during deep sleep with delta waves of up to 75V.

Alpha waves 30 are typically generated at 8 to 12 Hz, and are schematically shown in FIG. 3. Beta Waves 32 are typically generated at 13 to 24 Hz, and schematically shown in FIG. 4. Alpha and beta waves 30, 32 are considered to be faster wave patterns. Theta waves 34 are typically generated at 4 to 7 Hz., and schematically shown in FIG. 5. Delta waves 36 are typically generated at 0.5 to 3 Hz, and typically occur during deep sleep. Delta waves 36 are schematically shown in FIG. 6. Theta waves and Delta waves 34, 36 are considered to be slow wave patterns. The electric signal sent by the electrode sensor 15 to the memory means 22 is preferably limited to 0.1 Hz to 45 Hz.

The definition of various sleep stages is based on detailed research of conventional EEG patterns, based upon a healthy adult. Each individual generates unique brain wave patterns, which are tracked to define specific sleep stages. Electrode brain patterns are typically obtained by placing a plurality of electrodes (not shown) at selected locations upon a user's scalp 27, and then recording the rhythmic bioelectric signals radiating from a user's brain 19.

In contrast, this invention positions an electrode sensor(s) 15 upon the user's neck near the brain stem 24 in proximity to the posterior aspect of the user's superior cervical region, in an area that is immediately inferior to the cranial cavity to electromagnetically stimulate the brain stem, to influence a desired mental state.

Preferably, a selected user's bioelectric brain signal 16 is non-invasively recorded 21 with at least one electrode 15 placed upon the user's neck 25 near the brain stem 24. The bioelectric brain signal 16 from the electrode sensor(s) 15 is recorded and remotely selectively streamlined 20, and the streamlined signal 20 is then selectively played back on demand, to one or more electromagnets 39 positioned upon a neck apparatus 70 worn about the user's neck 25 in a manner to position the electromagnet(s) 39–42 in proximity to the brain stem 24, to influence a desired mental state.

For example, a streamlined sleep state 85 will now be discussed in detail.

There are four known stages of sleep:

Stage 1 sleep is considered the lightest stage of sleep, and comprises low voltage, regular activity ranging from 3 to 7 Hz, and lasts up to 5 percent of a normal adult sleep cycle. Stage 1 sleep is shown in FIG. 5.

Figure 4:
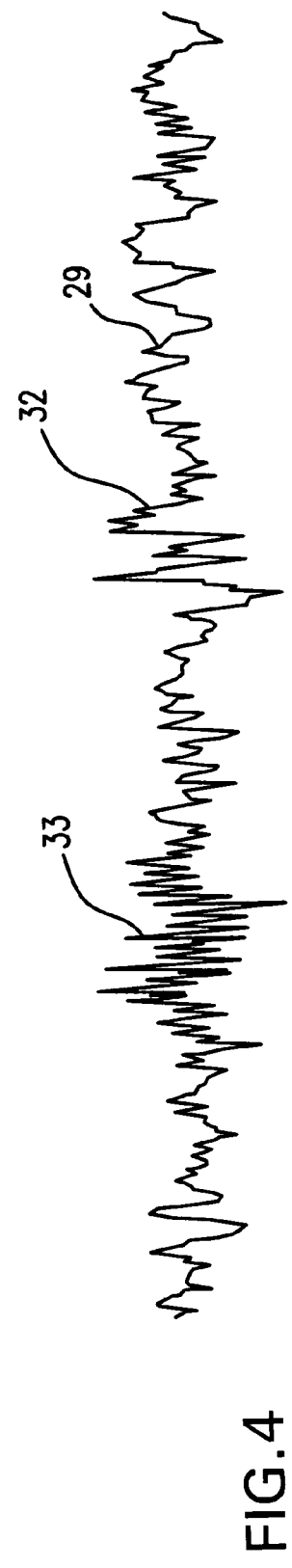
FIG. 4 is a schematic view of a portion of a Beta brain wave pattern of 13 to 18 Hz, taken adjacent to the user's skull, showing sleep spindles.

Stage 2 sleep is characterized by frequent sleep spindles 33 ranging from 12 to 14 Hz, and further characterized by triphasic waves called K complexes (not shown). Stage 2 sleep, also includes sleep spindles 33, which are shown in FIG. 4. Stage 2 sleep typically lasts up to 45 percent of a normal adult sleep cycle.

Stage 3 sleep is characterized by high voltage activity at 0.5 to 3 Hz, known as Delta wave 36 activity, which occupies less than 50 percent of a typical brain wave tracing, and lasts up to about 12 percent of the normal adult sleep cycle. Stage 3 sleep and stage 4 sleep are shown in FIG. 6.

Stage 4 sleep is characterized by Delta waves 36, which occupy more than 50 percent of the brain wave tracing. Stage 4 sleep lasts up to about 13 percent of the normal adult sleep cycle.

Figure 2:
FIG. 2 is a schematic view of a portion of a typical EEG brain wave pattern taken adjacent to the user's skull when the user is awake, showing low voltage, random, fast signals.
Figure 7:
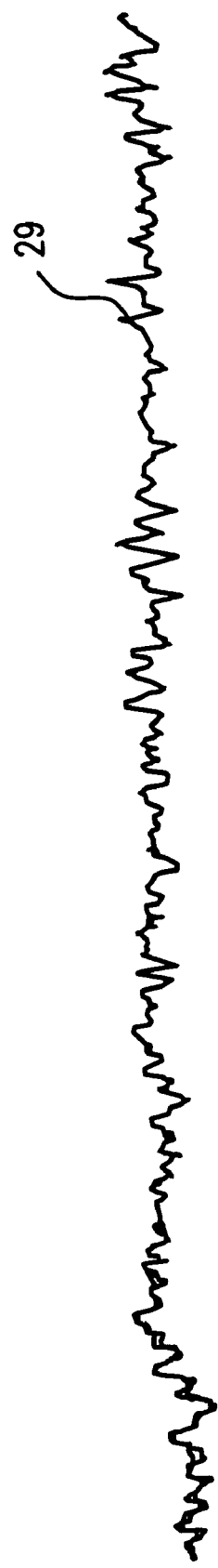
FIG. 7 is a schematic view of an EEG tracing taken adjacent to the user's skull, showing random, fast sawtooth waves found during REM sleep.
Figure 8:
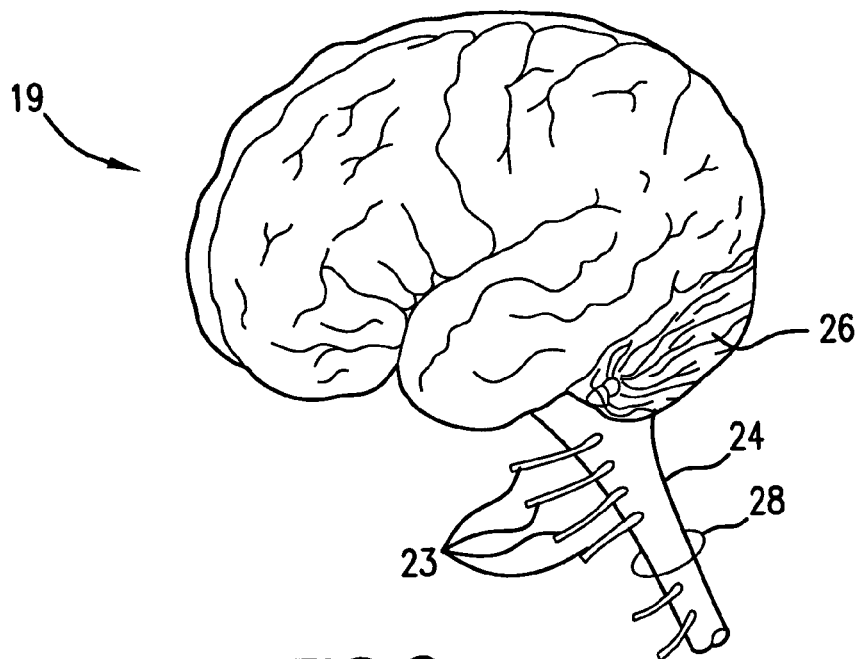
FIG. 8 is a diagram of a brain, showing the location of the cerebellum, the brain stem, cranial nerves, and the foramen magnum, wherein the user's skull in not shown for clarity.
Figure 9:
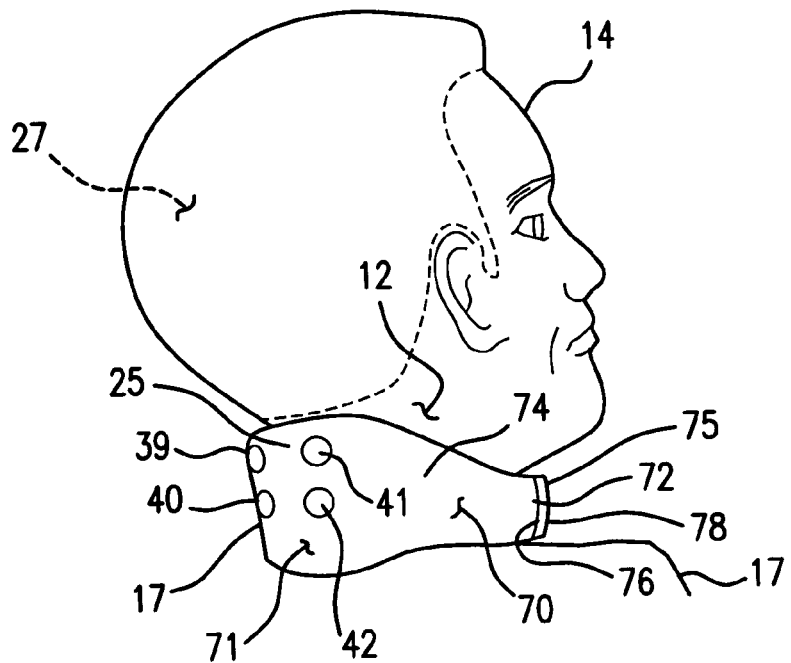
FIG. 9 is a perspective view of a user wearing the neck apparatus with multiple electromagnets positioned on the neck adjacent to the brain stem.
Figure 10:
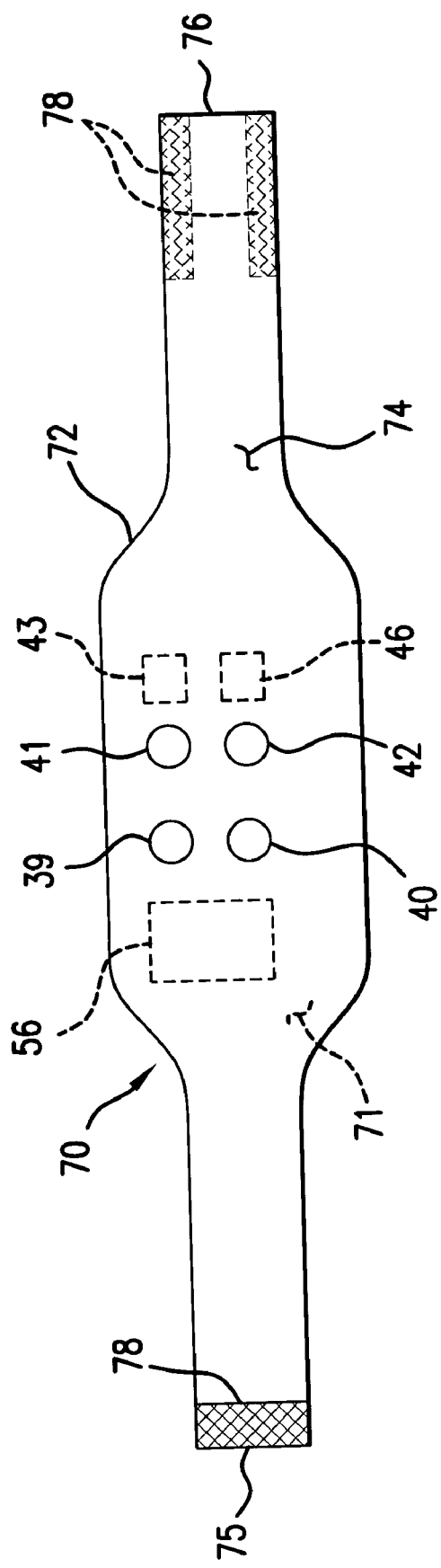
FIG. 10 is a plan view of the inner side of the neck apparatus, showing the preferred location of multiple electromagnets.

REM (Rapid Eye Movement) sleep 61, comprising low voltage, is characterized by random, fast waves interspersed with sawtooth waves 29 is shown in FIG. 7. REM sleep patterns 61 occur during dreaming, and at times include spike signals up to 45 Hz. NREM (non-rapid eye movement) sleep 62 is characterized by low voltage, random, fast waves similar to those shown in FIG. 2.

Elderly sleep cycles may not correspond with the normal adult sleep cycles noted above. Children's sleep cycles also vary, and thus elderly sleep cycles and children's sleep cycles will require a customized sleep cycle, unique to a selected user.

The brain wave recording means 21, used for monitoring and storing brain wave patterns, including 0.1 Hz to 45 Hz brain wave patterns, is well known to one skilled in this art, and thus is not further detailed herein.

The user's brain stem 24 produces minute bioelectric signals 16, which form rhythmic patterns. The electromagnet(s) 39 are actuated to influence these minute bioelectric signals 16, which are received by the brain stem 24 and sent to various control centers located deep in the user's brain 19. These minute bioelectric signals 38 may be adapted to influence, or hypnotize a user into one or more selected streamlined brain wave patterns 20.

This invention converts these bioelectric signals 16 to a streamlined brain wave pattern 20, which is then streamlined and sent to the electromagnet(s) 39 to create complimentary minute magnetic signals 38, which are easily transmitted to the brain stem 24 from a location positioned upon the user's neck 25 near the brain stem 24 in close proximity to the posterior aspect of the user's superior cervical region, in an area that is immediately inferior to the cranial cavity to electromagnetically stimulate the brain stem, to influence a desired mental state.

Both REM sleep patterns 61 and NREM sleep patterns 62 are included in the streamlined 20 sleep pattern 86, ensuring that the user obtains the benefits of both REM 61 and NREM 62 sleep patterns during the streamlined 20 sleep cycle 86, disclosed herein.

In a healthy adult, NREM sleep 62 occurs during about 75 percent of a sleep cycle. REM sleep 61 occurs in about 25 percent of a sleep cycle.

In the present invention, stage one sleep is preferably reduced to one-to-five minutes of the streamlined sleep cycle 86; stage two sleep is preferably reduced to about 45 to 70 minutes of the streamlined sleep cycle 86; stage three sleep is preferably reduced to 30 to 50 minutes of the streamlined sleep cycle 86; and stage four sleep is preferably reduced to 40 to 120 minutes of the streamlined sleep cycle 86. This provides the user with a total streamlined 20 sleep cycle 86 of two to three hours duration, while including all four stages of a conventional sleep cycle, including both REM 61 and NREM 62 sleep.

Transitional modulation between the four stages of sleep is also preferably streamlined 20 and selectively incorporated into the transition between adjacent sleep stages.

The user 14 will awake from the streamlined sleep cycle 86 refreshed and invigorated, as the streamlined 20 sleep cycle 86 will override most external distractions, which often disturb a restful sleep cycle. Thus, in two to three hours of streamlined 20 sleep, the user will awake relaxed, refreshed and ready to "seize the day". After approximately 8 hours of work or play, the user 14 may use the magnetic brain wave stimulation apparatus 100 disclosed herein obtain a second streamlined 20 sleep cycle 86 in the next two to three hours. The user 14 will then awake relaxed and refreshed a second time in a 24 hour period, enabling the user 14 to work or play a second 8 hours, fully refreshed by the equivalent of a full night's sleep. This leaves an additional two to four hours for personal time, ensuring two full eight hour shifts in a 24 hour period, at the user's 14 current strength, vitality, age, knowledge and attentiveness.

The magnetic brain wave stimulation apparatus 100 will aid user's who are long sleepers, to make more efficient use of their time and energy. People who have insomnia or trouble sleeping will also be helped. Productivity will be increased, perhaps even doubled, and the extra time, at current strength and vitality, will greatly enhance a user's 14 ability to get things done on time.

By working two full eight hour shifts within 24 hours, the number of workers needed for a specific or prolonged task is significantly reduced, which in return reduces the infrastructure and the quantity of supply items required for a specific or prolonged task.

While the magnetic brain wave stimulation apparatus 100 has been disclosed herein, for use as a streamlined sleep apparatus 86, other mental states may likewise be influenced and replicated. The magnetic brain wave stimulation apparatus 100 disclosed herein, may be readily adapted to influence a streamlined 20 sleep state 86; a streamlined 20 calm and relaxing state 88; a streamlined 20 creative mental state 90; or a streamlined 20 stimulated mental state 92, to suit the needs of the intended user 14.

It is well known to one skilled in the art, that every electrical field 37 has a corresponding magnetic field 38 oriented at right angles to the electrical field 37. Thus, pre-recorded electrical signals 37 from brain waves may be readily streamlined 20 and sent to a magnetic signal 38 positioned at right angles to the electrical signal 37. Electromagnet(s) 39–42 generate a magnetic signal 44 when electrically energized, and these magnetic signals 44 are synchronized to correspond with the user's 14 streamlined 20 brain wave pattern. The magnetic signal 44 is selectively actuated, as the electrical signal 37 selectively energizes the coil 45 surrounding the ring portion 48 electromagnet 39.

Multiple electromagnets 39–42 may be used, for example, one for the slow wave patterns, and another for the faster wave patterns.

Where only one electromagnet 39 is used, the streamlined signals are selectively streamlined 20 and then transmitted to energize the electromagnet 39 in a frequency range of from 0.1 Hz to 45 Hz. Of course, more than four electromagnet(s) 39–42 may also be used to suit specific user preference.

The electromagnet(s) 39–42 disclosed herein are preferably ring type electromagnet(s) 39 having a circular ring portion 48 upon which an electrical coil 35 is wound. A ferrous core 44 is positioned within the circular ring portion 48. The ferrous core 44 vibrates within the electrical coil 35 responsive to the electric signal 37 to create the corresponding magnetic signal 38, which is generated at right angles to the electrical signal 37.

The electromagnet 39 becomes weaker or stronger as the voltage to the electromagnet(s) 39–42 varies. For example, the earpiece in a conventional telephone comprises an electromagnet 39 with a ferrous core 44. The stronger the current, the further the ferrous core 44 moves, to create soundwaves of different frequencies. Thus one electromagnet 39 may transmit a magnetic signal 38 in the range of 0.1 Hz to 45 Hz, or cycles per second, to correspond to the prerecorded and streamlined 20 brain wave patterns incorporated within the selected brain wave signal.

The streamlined 20 brain wave pattern may be transmitted by one or more analog or digital transmitters 50 to one or more remote receiving means 56. Any known transmitting means 52 may be used. Likewise, any known receiving means 56 may be used. The streamlined 20 electrical signals 37 are selectively transmitted to one or more wireless receiving means 56 located adjacent to the neck apparatus 70. The wireless receiving means 56 transfers the wireless signal 60 to a selected electromagnet 39–42, which generates a magnetic field 38, at right angles to the electrical field 37 recorded by the brain wave recording apparatus 18, as shown in FIG. 1.

Alternately, the prerecorded streamlined brain wave pattern 20 may be sent directly to the electromagnet(s) 39–42, eliminating the need for the transmitter 50 and receiver 56, as shown in FIG. 12.

The magnetic pulse generated by the magnetic field 38 is transmitted from the electromagnet(s) 39–42 to non-invasively penetrate through the skin 12 of the user's 14 neck 25 to the brain stem 24, at the frequencies and cycles per second selected from the range of from 0.1 Hz to 45 Hz corresponding to the streamlined brain wave patterns 20 previously recorded. Cranial nerves 23 in the user's neck 25 aid in transmitting the magnetic signals 38 to the brain stem 24.

Because magnetic signals 38 from the electromagnet 39 are used to induce a desired mental state, no salves, ointments or adhesives are required on the user's skin adjacent to the electromagnet 39, as are typically required with electrical apparatus in contact with the user's skin. This greatly simplifies application of the neck apparatus 70 upon the user's neck 25, and small movement of the electromagnet 39 in relation to the user's skin 12 during use does not adversely affect the magnetic signal 38 to the brain stem 24.

The transmitting 50 and receiving means 56, when used, are preferably wireless, so that a user 14 does not get tangled in electrical cords (not shown) while wearing the neck apparatus 70.

A switch means 43 accessible to the user 14 is preferably used to selectively actuate and turn off the magnetic brain wave stimulation apparatus 100.

A power storing or generating means 46, such as a battery or small electric generator, may be positioned on the therapeutic neck apparatus 70 to selectively provide electric current to the electromagnet(s) 39–42, responsive to the streamlined 20 brain wave patterns. The streamlined 20 magnetic brain wave patterns generated by the electromagnets 39–42 are transmitted non-invasively through the skin 12 on the user's neck 25 adjacent to the brain stem 24, which distributes the streamlined 20 brain wave patterns to a user's brain control centers (not shown), to influence a desired mental state.

The neck apparatus 70 preferably comprises a removable collar 72 sized to be placed about the user's neck 25. The removable collar 72 is preferably made of a fabric 74, soft foam or other non-conductive, flexible material, for comfort. The first and second distal ends 75, 76 of the removable collar 72 are preferably releasably and adjustably secured with a suitable securement means 78, such as hook and loop type fasteners. The neck apparatus 70 is positioned and secured about the user's neck 25 in a manner to avoid difficulty with breathing, during use. One or more electromagnet(s) 39–42 are positioned on the therapeutic neck apparatus 70 to be in close contact with the user's skin 12 on the user's neck 25 in proximity to the posterior aspect of the user's superior cervical region, in an area that is immediately inferior to the cranial cavity to stimulate the brain stem 24, to more effectively transmit the magnetic signals 38 generated by the electromagnet(s) 39–42 to the brain stem 24.

Cranial nerves 23 located within the skin 12 in proximity to the user's neck 25 aid in directing the magnetic pulses 44 to the brain stem 24. No adhesive, oil, grease, paste or gel is required to transmit the magnetic field 38 generated by the electromagnet(s) 39–42, as is typically required when placing electrical signal equipment upon a user's skin 12.

The magnetic pulse signals 38 generated by the electromagnet(s) 39–42 are of a very low threshold, in a range of from 1 to 24 Gauss rating, similar to the electromagnetic coils used in cell phones and wireless headphones. Thus, the magnetic pulse signals 38 pose no more threat to the user than conventional cell phones or wireless headphones in common use today.

Alternately, a cap or headband or other clothing (not shown) may be used to adequately position the electromagnet(s) 39 in position on the user's neck 25. The electromagnets 39–42 are positioned on the cap, clothing or headband to closely align with the back of the neck 25 at a location in close proximity to the posterior aspect of the user's superior cervical region, in an area that is immediately inferior to the cranial cavity. As previously noted, one or more electromagnet(s) 39–40 may be used generate a plurality of overlapping, dynamic magnetic signals 38, to selectively influence the user's 14 brain wave pattern. Prerecorded brain wave signals are preferably streamlined 20, then recorded, selectively deleted and repeated, and then played back to the selected user 14 for use in influencing a desired mental state.

Alternately, streamlined 20 computer generated signals may be used to simulate desired brain wave signals in the range of from 0.1 Hz to 45 Hz, or multiple brain wave patterns may be summed and streamlined 20 for use with this magnetic brain wave stimulation apparatus 100, to induce a selected and desired mental state.

Preferably, separate streamlined brain wave patterns 20 are recorded and stored for each selected mental state. The user 14 may then select the desired mental state, such as a shortened sleep state 86, a relaxed mental state 88, a stimulated mental state 92 or a creative state 90, prior to use.

Separate frequencies may be used to transmit the brain wave patterns from the transmitting means 52 to the wireless remote receiver 60. The signals received by the wireless remote receiver 60 are then sent to the electromagnet(s) 39.

Small magnetic signals 38 generated by the electromagnet(s) 39–42 are non-invasively transmitted through the user's skin 12 located on the user's neck 25, which penetrate to the brain stem 24, and through the brain stem 24 to the control centers located within the user's brain 19. These small magnetic signals 38 serve to influence the control centers by creating a streamlined 20 brain wave pattern, to selectively produce a desired metal state.

The streamlined 20 brain wave pattern influences the brain centers into the desired mental state, while ignoring the many external distractions that typically occur. When used to induce sleep, the streamlined 20 brain wave sleep state 86 serves to shorten the tentative transitions between various sleep stages, and more efficiently focuses the sleep centers to obtain a more complete and restful sleep. The brain wave pattern may be streamlined 20 to create a sleep cycle of two to three hours, or to obtain a heightened creative mental state 90 for a sustained period of time. Other uses include influencing a sustained relaxed state 88, or influencing a heightened stimulated state 92, depending upon the specific streamlined 20 brain wave pattern transmitted to the electromagnet(s) 39–42.

The neck apparatus 70 may be padded 71 to provide a comfortable fit about the user's neck 23 above the shoulders 17. The padding 71 may further serve to protect the electrical circuitry (not shown) located on the therapeutic neck apparatus 70. Additionally, the padding 71 may serve as a small pillow, which remains with the user 14 while sitting, standing, turning, moving or lying down.

It is well known that a person hypnotized into a deep sleep for several hours awakes in a rested, relaxed and energized condition. The streamlined brainwave pattern 20 utilized herein may be used to produce similar results, while eliminating the need to be hypnotized during each sleep cycle. The improved efficiency of a two to three hour sleep cycle enables a user to perform at maximum efficiency for two separate and distinct eight hour periods in a 24 hour day. Thus, it is anticipated that a given task requiring several days, weeks or months, can be accomplished in significantly less time than possible with a user's normal, unassisted sleep cycle.

Drugs and medication are at times used to extend a user's 14 mental state, or to induce sleep. These drugs and medication often have adverse side effects which affect the alertness, efficiency and competence of the user 14. The streamlined magnetic brain wave stimulation apparatus 100 disclosed herein is non-invasive, and provides significant beneficial results, without the use of drugs or medication.

For example, a sustained stimulated mental state 92 may be induced during extended periods of time, to extend the user's 14 ability to perform prolonged tasks, such as long distance flying or long distance driving.

Referring now to FIG. 1, a transmitting apparatus 50 includes a streamlined brain wave pattern 20 transmitting means 52, which generates an analog or digital electrical signal 37 responsive to the streamlined 20 brain wave pattern stored in the memory means 22. The transmitting means 52 is preferably wireless, and may include any known transmitting means 52, such as audible, visual, electrical, magnetic, radar, sonar, ultrasonic, subsonic, radio waves, etc.

The transmitted streamlined 20 brain wave signal comprises one or more distinct electronic signals 37 received from the memory means 22. Typical human hearing is in the range of 20 to 20,000 Hz. Signals ranging from 0.1 up to 20 Hz, typically fall below the hearing threshold of a normal human ear. Thus, these signals may be transmitted as either audible or non-audible sounds. However, the streamlined 20 brain wave signals are preferably not audibly transmitted, so that brain wave patterns up to 45 Hz may be transmitted to the selected user 14.

The transmitted electronic signals 54 are received by one or more wireless receiving means 56 preferably located on the therapeutic neck apparatus 70. When the streamlined 20 brain wave pattern is stored directly upon the neck apparatus 70, the electronic signal 37 generated by the streamlined 20 brain wave pattern may be sent directly to the electromagnet(s) 39–42. The received electronic signal 54 is sent to one or more electromagnet(s) 39–42, which convert the plurality of electronic signals 54 to a plurality of complimentary magnetic signals 38. The frequency, pulse duration, and intensity of the magnetic signals 38 all contribute to the amount of neuronal stimulation generated by the electromagnet(s) 39–42.

The magnetic field 38 generated by the electromagnet(s) 39–42 are not of an intensity to be felt or consciously observed by the user 14. Preferably, the magnetic signal 38 is no stronger than the magnetic signal 38 generated by a cell phone or a wireless speaker (not shown). The streamlined brain wave patterns 20 may be compressed for storage, and decompressed to their original form at the time of use. Techniques for compression and decompression are well known in the art, and any known compression and decompression means may be used. Compression techniques serve to reduce the volume and amount of data storage required.

The therapeutic neck apparatus 70 fits comfortably about the user's neck 25 above the user's shoulders 17, allowing the user 14 to freely move, turn, sit, stand or lay down.

A power generating or storage means 46, such as a battery or generator, is preferably positioned on the therapeutic neck apparatus 70, and used to energize the electromagnet(s) 39–42. A switch means 43 may be provided between the power storage means 46 and the electromagnets 39–42, to selectively actuate the electromagnet(s) 39–42. A computer chip (not shown) may alternately be used to control and direct the electrical signal 54 to the electromagnet(s) 39–42.

Protective circuitry known in the art (not shown) may also be used to inhibit excessive electronic or magnetic signals 54, 38, to ensure safe use of this magnetic brain wave stimulation apparatus 100, under varying conditions.

The streamlined 20 brain wave pattern is preferably customized for a specific user 14, and is preferably protectively coded 66, encrypted, or otherwise customized to create no signal, or a random or disruptive signal when a different user attempts unauthorized use of the customized magnetic brain wave stimulation apparatus 100 disclosed herein. This serves as a safeguard against unauthorized use. Any known encryption 66 means may be used.

Alternately, a plurality of selected brain wave signals may be summed and streamlined, to create a generalized or computerized streamlined 20 brain wave pattern, which may be adapted for use by more than one selected user. This serves to standardize and reduce the cost of customized streamlined brain wave patterns 20, which may not work for all individual users, particularly among young, adult and senior users. However this technology may be adapted for selected groups of users 14.

It is also within the scope of this disclosure to record the streamlined brain wave pattern 20 on a computer chip, memory stick, or other known compact memory storage means 22, enabling the streamlined brain wave pattern 20 to be positioned directly onto the therapeutic neck apparatus 70. This will eliminate the need for a transmitter 50 and a wireless receiver 60, with resulting cost, weight and space savings.

As previously noted, this same invention may be used to provide a sustained creative state 90. In this embodiment, the brain wave recording equipment is used to record the user 14 while in a heightened creative mental state 90. The creative state brain wave patterns are pre-recorded and streamlined 20 as previously noted. The streamlined 20 pattern is then transmitted or otherwise sent to the electromagnets 39–42, when an extended creative mental state 90 is desired. The creative mental state 90 thus streamlined 20 and recorded 21, will substantially reduce "writer's block", and increase the productivity and attention span during any creative endeavor, and may be used to sustain the creative mental state 90 for a prolonged duration.

This invention may alternately be used to produce a heightened stimulating mental state 92, by recording 21 the user's brain wave pattern 20 during a heightened stimulating mental state 92, and sending the streamlined 20 recorded 21 signal to the selected electromagnet(s) 39–42, on demand.

Alternately, a user 14 may be transported to a restful and calm mental state, by pre-recording and streamlining 20 a calming brain wave signal, and sending the streamlined 20 recorded calming signal to the selected electromagnets 39–42 positioned upon the user's neck as previously noted.

The use of a pre-recorded streamlined brain wave pattern 20 to selectively heighten, maintain and streamline 20 a selected mental state, may be adapted for many uses, and recorded 21 and played back when desired. Such alternate uses are intended to fall within the scope of this disclosure, and the accompanying claims.

The use of a convenient memory means 22, such as a computer disc or memory stick, enables the user 14 to easily adapt the magnetic brain wave stimulation apparatus 100 to a variety of selected uses and applications, by simply replacing or selecting one pre-recorded memory means 22 for another pre-recorded memory means 22.

The scope of the present invention is not strictly limited to the specific embodiments disclosed herein. The invention may be practiced by one skilled in this art by utilizing numerous features and adaptations practiced in the art. Such features and adaptations are intended to be included within the scope of this disclosure, and the accompanying claims.

PARTS LIST

100—Streamlined magnetic brain wave stimulation apparatus
12—skin
14—user
15—electrode sensor
16—bioelectric signal
17—shoulders
18—brain wave recording apparatus
19—brain
20—streamlined brain wave patterns
21—recording device
22—memory means
23—cranial nerves
24—brain stem
25—user's neck
27—scalp
29—sawtooth waves
30—alpha brain wave signal
31—low voltage, random, fast, awake brain wave pattern
32—beta brain wave signal
33—sleep spindles
34—theta brain wave signal
35—coil
36—delta brain wave signal
37—electrical signal
38—magnetic signal 39—first electromagnet
40—second electromagnet
41—third electromagnet
42—fourth electromagnet
43—switch means
44—ferrous core
46—power storing or generating means
48—ring portion
50—transmitter
52—transmitting means
54—transmitted electronic signals
56—wireless receiving means
60—wireless rhythmic signal
61—REM Sleep
62—NREM Sleep
64—playback apparatus
66—protectively coded or encrypted
70—neck apparatus
71—padding
72—removable collar
74—fabric
75—first distal end
76—second distal end
78—securement means
80—first piece of brain wave data
81—second end of first piece
82—second piece of brain wave data
84—third piece of brain wave data
85—first end of third piece
86—sleep state
88—calm and relaxing state
90—creative mental state
92—stimulated mental state

We claim:

1. An apparatus to influence the mental state of a selected user, which comprises:
   a) positioning at least one electrical sensor upon a user's neck near the brain stem in proximity to the posterior aspect of the user's superior cervical region, in an area that is immediately inferior to the cranial cavity;
   b) recording the selected user's brain wave signal from the at least one electrical sensor to a suitable memory means;
   c) modifying said pre-recorded brain wave signal by identifying and selectively recording, deleting and repeating selected portions of the pre-recorded brain wave signal, to create a streamlined brain wave signal;
   d) storing said streamlined brain wave signal for subsequent use by said selected user;
   e) selectively actuating said streamlined brain wave signal, to produce an electrical signal for transmission to at least one electromagnet; to produce a corresponding streamlined magnetic signal at right angles to said electrical signal; and
   f) positioning said at least one electromagnet upon a removable neck apparatus positioned upon a selected user's neck, near to the user's brain stem in proximity to the posterior aspect of the user's superior cervical region, in an area that is immediately inferior to the cranial cavity; and
   g) selectively controlling the intensity, frequency and duration of the streamlined brain wave signal to influence the desired mental state of the user.

2. The apparatus of claim 1, comprising recording a selected user's brain wave signal within a selected frequency range of from 0.1 Hz to 45 Hz, and streamlining said brain wave signal to influence a desired mental state.

3. The apparatus of claim 1, wherein the electromagnet is a ring type electromagnet with a ferrous core similar to the ring type electromagnets used in cellular telephones.

4. The apparatus of claim 1, wherein the streamlined brain wave signal is transmitted from a remote location to a receiver located on the neck apparatus, and a corresponding electric signal is transferred from the receiver to at least one electromagnet located upon the neck apparatus.

5. The apparatus of claim 1, wherein the neck apparatus is adjustably secured about the user's neck with a hook and loop type fabric to adjustably conform to the size of the user's neck to ensure a comfortable fit about the user's neck, during use.

6. The apparatus of claim 1, wherein the pre-recorded brain wave signal of said user is identified, selected, deleted, and repeated, then recorded to create a streamlined sleep signal, and the streamlined sleep signal is transmitted to at least one electromagnet located on said neck apparatus positioned about the user's neck, to influence the duration of said streamlined sleep state to at least one half the normal duration of the user's sleep state.

7. The apparatus of claim 1, wherein the pre-recorded brain wave signal of said user is identified, selected, deleted, and repeated, then recorded to create a streamlined creative signal, and the streamlined creative signal is transmitted to at least one electromagnet located on said neck apparatus positioned about the user's neck, to influence the duration of said streamlined creative state of a selected user for an extended duration.

8. The apparatus of claim 1, wherein the pre-recorded brain wave signal of said user is identified, selected, deleted, and repeated, then recorded to create a streamlined relaxing mental signal, and the streamlined relaxing mental signal is selectively transmitted to at least one electromagnet located on said neck apparatus positioned about the user's neck, to influence the duration of said streamlined relaxing mental state of a selected user for an extended duration.

9. The apparatus of claim 1, wherein the pre-recorded brain wave signal of said user is identified, selected, deleted, and repeated, then recorded to create a streamlined stimulated mental signal, and the streamlined stimulated mental signal is transmitted to at least one electromagnet located on said neck apparatus positioned about the user's neck, to influence the duration of said streamlined stimulated mental state of a selected user for an extended duration.

10. The apparatus of claim 1, wherein the streamlined brain wave signal is one of: an analog electrical signal, a digital electrical signal and a microwave signal.

11. The apparatus of claim 1, wherein the prerecorded streamlined brain wave signal is protectively coded to limit the use of the prerecorded streamlined brain wave signal for playback only by said selective user.

12. An apparatus to influence the mental state of a selected user, which comprises:
   a) recording a selected user's brain wave signal with at least one electric sensor positioned on a portion of a user's neck in proximity to the posterior aspect of the user's superior cervical region, in an area that is immediately inferior to the cranial cavity within a selected frequency range of from 0.1 Hz to 45 Hz, and storing said pre-recorded brain wave signal to a suitable memory means;
   b) modifying said pre-recorded brain wave signal by identifying, and selectively deleting and repeating selected portions of the pre-recorded brain wave signal, and recording the modified brain wave signal to create a streamlined brain wave signal;

c) selectively actuating said streamlined brain wave signal, to produce an electrical signal for transmission to at least one electromagnet located on the neck apparatus, to produce a corresponding streamlined magnetic signal at right angles to said electrical signal; and e) positioning said at least one electromagnet upon an adjustable and removable neck apparatus positioned upon a selected user's neck, near the user's skin in proximity to the user's brain stem in proximity to the posterior aspect of the user's superior cervical region, in an area that is inferior to the cranial cavity;

f) selectively controlling the intensity, frequency and duration of the streamlined brain wave signal to influence the desired mental state of the user; and protectively coding said streamlined brain wave signal to ensure use only by the intended user.

13. A method to influence the mental state of a selected user, which comprises:
   a) positioning an electrical sensor on the user's neck in proximity to the user's brain stem;
   b) pre-recording an electrical signal from the electrical sensor to a recording means;
   c) modifying said pre-recorded brain wave signal by identifying and selectively recording, deleting and repeating selected portions of the pre-recorded brain wave signal to create a streamlined brain wave signal;
   d) supporting at least one electromagnet upon a removable neck apparatus;
   d) positioning the neck strap apparatus upon a selected user's neck, thus positioning the electromagnet near the user's skin in proximity to the user's brain stem adjacent to the posterior aspect of the user's superior cervical region, in an area that is inferior to the cranial cavity;
   e) transmitting said streamlined brain wave signal as an electrical signal to said at least one electromagnet, to produce a corresponding streamlined magnetic signal at right angles to said electrical signal; and
   f) controlling the intensity, frequency and duration of the streamlined brain wave signal to influence the desired mental state of the selected user.

14. The method of claim 13, comprising selecting a portion of the electrical signal from the electrical sensor for recording within a frequency range of from 0.1 Hz to 45 Hz; and streamlining the recorded signal prior to use.

15. The method of claim 13, comprising transmitting said streamlined brain wave signal from a remote storage means via transmission waves to a receiving means located on the neck strap apparatus, and sending an electronic signal from the receiving means to the at least one electromagnet located upon the neck apparatus.

16. The method of claim 13, comprising selecting said at least one electromagnet with a ferrous core as a ring type electromagnet similar to the ring type electromagnets used in cellular telephones.

17. The method of claim 13, comprising adjusting the size of the removable neck strap apparatus with a hook and loop type fabric to conform to the size of the selected user's neck, to ensure a comfortable fit about the user's neck during use.

18. The method of claim 13 comprising identifying, selecting, deleting, repeating and recording a specific user's brain wave pattern to create a streamlined sleep signal, and transmitting said streamlined sleep signal to at least one electromagnet, and influencing the duration of said streamlined sleep state to at least one half the normal duration of the sleep state of said selected user.

19. The method of claim 13, comprising identifying, selecting, deleting, repeating and recording a specific user's brain wave pattern to create a streamlined creative signal, and transmitting said streamlined creative signal to at least one electromagnet, to influence the creative state of said selected user for an extended duration.

20. The method of claim 13, comprising identifying, selecting, deleting, repeating and recording a specific user's brain wave pattern to create a streamlined relaxing mental signal, and transmitting said streamlined relaxing mental signal to at least one electromagnet, to influence the relaxing mental state of said selected user for an extended duration.

21. The method of claim 13, comprising identifying, selecting, deleting, repeating and recording a specific user's brain wave pattern to create a streamlined stimulated mental signal, and transmitting said stimulated mental signal to at least one electromagnet, to influence the stimulated mental state of said selected user for an extended duration.

22. The method of claim 13, comprising transmitting the streamlined brain wave signal as one of: an analog electrical signal, a digital electrical signal and a microwave signal.

23. The method of claim 13, comprising pre-recording the streamlined brain wave signal for selective playback by the selected user, and protectively coding the prerecorded streamlined brain wave signal to limit the use of the pre-recorded streamlined brain wave signal for playback only by said selected user.

* * * * *